United States Patent [19]

Powell et al.

[11] 4,388,104

[45] Jun. 14, 1983

[54] 3-PHENYLMETHOXYTETRAHYDROPY-RAN HERBICIDES

[75] Inventors: James E. Powell, Ripon, Calif.; Michael D. Barker, Sittingbourne, England

[73] Assignee: Shell Oil Company, Houston, Tex.

[21] Appl. No.: 314,612

[22] Filed: Oct. 26, 1981

[51] Int. Cl.³ .................... A01N 43/00; C07D 309/10; C07D 309/12; C07D 317/08
[52] U.S. Cl. ........................................ 71/88; 549/397; 549/416
[58] Field of Search ................. 260/345.9 R, 340.9 R; 71/88; 549/416, 397

[56]  References Cited

U.S. PATENT DOCUMENTS 3,755,365  8/1973  Fentiman, Jr. et al. ..... 260/340.9 R
4,146,384  3/1979  Schmidt et al. .......................... 71/88
4,291,051  9/1981  Wilson et al. ................ 260/340.9 R

FOREIGN PATENT DOCUMENTS 2937645  4/1981  Fed. Rep. of Germany .

Primary Examiner—Nicky Chan

[57]  ABSTRACT

Certain 3-phenylmethoxytetrahydropyrans, useful as herbicides.

3 Claims, No Drawings

3-PHENYLMETHOXYTETRAHYDROPYRAN HERBICIDES

DESCRIPTION OF THE INVENTION

It has been found that useful herbicidal properties are exhibited by 3-phenylmethoxytetrahydropyrans described by the formula:

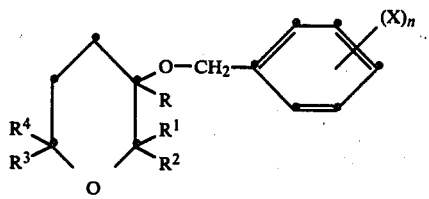

wherein R is hydrogen, phenyl or alkyl of from one to four carbon atoms, $R^1$ is hydrogen or alkyl of from one to four carbon atoms, $R^2$ is hydrogen, $R^3$ is hydrogen, alkyl of from one to four carbon atoms, phenyl or is a moiety $R^5$—O—$(CH_2CH_2$—O$)_{\overline{m}}$CH($R^6$)—, wherein m is zero, one or two, $R^4$ is hydrogen, alkyl of from one to four carbon atoms, or a moiety $R^5$—O$((CH_2CH_2)$—O$)_{\overline{m}}$CH($R^6$)—, $R^5$ is alkyl of from one to six carbon atoms and $R^6$ is hydrogen or alkyl of one to four carbon atoms, with the proviso that $R^3$ and $R^2$ together can represent the moiety —C($R^7$)$_2$—O—, $R^7$ being hydrogen or alkyl of from one to four carbon atoms and $R^2$ being the oxa (—O—) oxygen therein, X is halogen—i.e., chlorine, bromine and fluorine—or methyl, and n is zero, one or two.

In these pyrans, each alkyl moiety that is present can be of either straight-chain or branched-chain configuration.

Some of the compounds of Formula I can exist in the form of geometric isomers; all exist in the form of chiral isomers. Thus, the compounds exhibit cis/trans isomerism with respect to the moiety

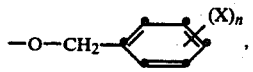

when $R^1$ is not the same as $R^2$, or $R^3$ is not the same as $R^4$, or one or both of $R^1$ and $R^2$ is different from one or both of $R^3$ and $R^4$. As is evident, quite complicated isomeric configurations can occur. Geometric isomerism also can occur when $R^3$ and $R^2$ together represent the —C($R^7$)$_2$O— moiety. In many cases, mixtures of isomers are obtained, and the individual isomers may not be easily isolated. The various isomeric forms and combinations thereof usually have different levels and spectra of herbicidal activity. For example, in those cases where one of $R^3$ and $R^4$ is other than hydrogen, the isomers having the cis configuration of the $R^3$ or $R^4$ moiety, with respect to the

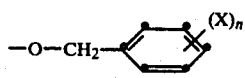

moiety, in most cases are more herbicidally active than are the corresponding trans isomers. This invention contemplates all of the herbicidally active isomers, as well as mixtures of isomers resulting from the synthesis methods used, and deliberately created mixtures.

The methods by which the compounds of Formula I can be synthesized and isolated are illustrated in Examples 1-20, hereinafter.

In general, the compounds are made by treating the corresponding tetrahydro-2H-pyran-3-ols with a halide,

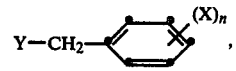

wherein Y is chlorine or bromine, in the presence of a strong base, such as sodium hydride, in a suitable inert solvent, such as N,N-dimethylformamide, N,N-dimethylacetamide, benzene, toluene, or the like. The conditions under which the treatment is conducted and the methods of recovery and purification of the product and separation of the isomers, are illustrated in the examples.

The precursor alcohols can be prepared by two general methods:

(1) treatment of the appropriate dihydropyran with a borane-tetrahydrofuran complex, and subsequent treatment of the resulting mixture with aqueous hydrogen peroxide under basic conditions. This method is exemplified in Examples 1 and 4.

Alternatively, the dihydropyran can be treated with borane-dimethyl sulfide complex in a solvent such as hexane, followed by adding an alcohol, such as ethanol, stripping the mixture of the solvent, dissolving the residue in a solvent such as tetrahydrofuran, then treating the mixture with aqueous hydrogen peroxide under basic conditions. This method is exemplified in Examples 5 through 17.

(2) treatment of the appropriate dihydro-2H-pyran-3(4H)-one with a Grignard reagent, R-Mg-halogen, to give the alcohol in which R is other than hydrogen (exemplified in Examples 2 and 3), or with lithium tri-sec-butyl borohydride in a solvent such as tetrahydrofuran, followed by addition of an alcohol, water, hydrogen peroxide and a base (exemplified in Examples 18–20).

Some of the dihydropyran precursors are known compounds. Others, wherein one of $R^3$ and $R^4$ is other than hydrogen, can be prepared from glutaraldehyde, as shown in Example 4, or from 3,4-dihydro-2H-pyran-2-methanol (Examples 5–10).

Where $R^3$ and $R^4$ each is other than hydrogen, the precursor can be prepared from acrolein dimer (Examples 11, 13, 14), or methacrolein dimer (Example 12). Where $R^3$ is other than hydrogen, and $R^4$ is hydrogen, the precursor can be prepared from the dimer of 3-buten-2-one (Examples 16 and 17).

Preparation of compounds of Formula I wherein $R^3$ and $R^2$ together represent the —C($R^7$)$_2$—O— moiety is illustrated in Examples 18–20. In this case, the precursor alcohol, also bearing a hydroxymethyl moiety on the carbon atom in the 6-position of the ring, is treated with an oxidizing agent such as m-chloroperoxybenzoic acid to effect the cyclization.

Recovery and purification of the intermediate and final products can be accomplished by conventional methods, as illustrated in the examples.

In many cases, the geometric isomers of the final products can be separated readily. In some cases, it may be found to be desirable to effect the separation by separation of the isomers of an intermediate, or a derivative, as in Example 4.

The following examples illustrate the methods which can be used for preparing compounds of Formula I. In each case, the identities of the final products, and each of the intermediates were confirmed by appropriate chemical and/or spectral analyses.

EXAMPLE 1

Tetrahydro-3-(phenylmethoxy)-2H-pyran (1)

In a first flask, 56.80 g of boron trifluoride etherate was added drop by drop over a two-hour period to a suspension of 11.40 g of sodium borohydride in 100 ml of dry diglyme, at room temperature. The reaction was slightly exothermic at first. The gas that was generated was allowed to pass through a trap containing 0.6 g of sodium borohydride in 50 ml of diglyme and then into a second flask (at −5° C. to +2° C.) containing 25.2 g of distilled 3,4-dihydro-2H-pyran dissolved in 250 ml of tetrahydrofuran. When all of the boron trifluoride etherate had been added to the first flask, the mixture therein was warmed to 60° C. and held there for one hour. Then the flask was disconnected. The cold mixture in the second flask was stirred for two hours. Then, at −15° C. to +8° C., 160 ml of 10% sodium hydroxide solution was added drop by drop. The reaction was very exothermic and required intensive cooling. The temperature of the mixture was allowed to rise to 40°–50° C. and 103 ml of 30% hydrogen peroxide solution was added drop by drop. The mixture then was warmed to and held at 55° C. for one hour. The mixture was held in a refrigerator overnight, then was saturated with potassium carbonate. Two layers resulted; they were separated and the aqueous layer was extracted with ether. The organic phases were combined, dried ($MgSO_4$), and the solvents were evaporated under reduced pressure. The residue was dissolved in methylene chloride, the solution was dried ($MgSO_4$) and the solvent was evaporated under reduced pressure. The residue was vacuum distilled to give tetrahydro-2H-pyran-3-ol (1A), as a liquid, b.p.: 55° C., 4 Torr.

1.48 g of a 57% oil dispersion of sodium hydride was washed with pentane to remove the oil and the sodium hydride was suspended in 10 ml of dimethylformamide. Under a nitrogen atmosphere at 1° C., the suspension was stirred while a solution of 3.00 g of 1A in 15 ml of dimethylformamide was added drop by drop. The mixture was allowed to warm to room temperature and held there for about 1.5 hours, then was cooled to 3°–4° C., and a solution of 3.72 g of benzyl chloride in 5 ml of dimethylformamide was added. The mixture was stirred for one hour, then partially stripped of solvent, and the residue was held in a refrigerator overnight. Then most of the solvent was stripped and the residue was stirred in a mixture of equal volumes of water and methylene chloride. The two phases were separated; the aqueous phase was brought to pH 7 with 6 N hydrochloric acid, and extracted with methylene chloride. The organic phases were combined, washed with saturated sodium bicarbonate solution, then with saturated sodium chloride solution, dried ($MgSO_4$) and stripped of solvent. The residue was distilled. 1 was obtained as the fraction boiling at 76° C., 0.1 Torr.

EXAMPLE 2

Tetrahydro-3-methyl-3-(phenylmethoxy)-2H-pyran (2)

53.78 g of pyridinium chlorochromate was stirred in 230 ml of methylene chloride under a nitrogen atmosphere at room temperature, and a solution of 11.97 g of 1A in 20 ml of methylene chloride was added to the stirred mixture. After 17 hours at room temperature, the mixture was diluted with twice its volume of anhydrous ether, and the resulting liquid phase was decanted, passed through a florisil filter and stripped of solvent. The residue was vacuum distilled, the fraction boiling at 70° C., 22 Torr, being dihydro-2H-pyran-3(4H)-one (2A).

13.5 ml of 3 M methyl magnesium bromide in ether was added drop by drop to a stirred solution of 4.00 g of 2A in 22 ml of tetrahydrofuran under a nitrogen atmosphere at −55° C.—−47° C. Over a two-hour period, the resulting mixture was allowed to warm to room temperature. 10 ml of saturated ammonium chloride solution was added, and 15 minutes later the organic phase was separated, dried ($MgSO_4$) and stripped of solvent to give residue A. The aqueous phase was partially stripped of water and extracted with methylene chloride; the extract was dried ($MgSO_4$) and stripped of solvent to give residue B. Residues A and B were combined and distilled. The fraction boiling at 55° C., 5.5 Torr., was identified as tetrahydro-3-methyl-2H-pyran-3-ol (2B).

2 was obtained as a pale green liquid, boiling point not determined, by treating 2B with benzyl chloride according to the procedure described for converting 1A to 1.

EXAMPLE 3

Tetrahydro-3-phenyl-3-(phenylmethoxy)-2H-pyran (3), was prepared as a liquid, b.p.: 130° C., 0.07 Torr., from phenyl magnesium chloride by the procedures described in Example 2.

EXAMPLE 4

Tetrahydro-2-phenyl-5-(phenylmethoxy)-2H-pyran cis isomer (4)

300 g of magnesium sulfate was added in portions to a mixture of 400 ml of 25% aqueous glutaraldehyde in 1200 ml of toluene, at 8°±3° C. The mixture then was stirred and filtered. The filtrate was refluxed to remove traces of water, then was Claisen-distilled to give a purified glutaraldehyde (4A).

136.1 ml of a 3 M solution of phenyl magnesium bromide in ether was added, drop by drop, to a solution of 37.1 g of 4A in 375 ml of tetrahydrofuran at −60°±10° C. The mixture was allowed to warm (over a two-hour period) to room temperature. Then 75 ml of a saturated solution of ammonium chloride in water was added, the temperature of the mixture being held at 0°–5° C. The mixture was stirred for 15 minutes, then the supernatant oil was decanted, dried ($MgSO_4$), and stripped of solvent. The residue was passed through a short column of silica gel using ethyl acetate as eluent. The eluate was stripped of solvent, and the residue was chromatographed (high pressure liquid) over silica gel, using as eluents one liter each, in sequence, of six mixtures of ethyl acetate and hexane, varying in content from 30% to 75% ethyl acetate, followed by two liters of ethyl acetate alone. Fractions 7 through 12 (in order of increasing polarity) were combined and stripped of solvent. The resulting solid was recrystallized from hexane to give tetrahydro-6-phenyl-2H-pyran-2-ol (as a mixture of diastereomers) (4B), as a solid, m.p.: 64.5°-71° C.

1.62 g of triethylamine was added to a solution of 14.24 g of 4B in 150 ml of toluene at room temperature. Then 19.04 g of phenyl isocyanate was added. The mixture was refluxed for 20 hours and filtered. The filtrate was stripped of solvent and the residue was mixed with 250 ml of hexane and filtered. The solvent was stripped from the filtrate. The residue was distilled through a short path bantamware head to give 2-phenyl-3,4-dihydro-2H-pyran (4C), as a liquid, b.p.: 62°-65° C., 0.15 Torr.

11 ml of a 1 M solution of borane in tetrahydrofuran was added drop by drop over a 20-minute period to a solution of 4.8 g of 4C in 20 ml of tetrahydrofuran at 4°-7° C. The resulting solution was stirred at 0°-5° C. for 3.5 hours, then at 25° C. over a weekend. An additional 5.5 ml of 1 M borane in tetrahydrofuran was added, and the mixture was stirred for one hour. 6.6 ml of 10% aqueous sodium hydroxide was added drop by drop at 5°-10° C. Then 3.4 ml of 30% hydrogen peroxide solution was added drop by drop at 37°-42° C. The mixture was stirred for one hour at 50° C., then cooled to 25° C., and 10 g of potassium carbonate was added. The mixture was stirred for one hour; then the organic phase was separated, dried (Na2SO4), and placed in a refrigerator. The solvent was evaporated under reduced pressure, the residue was dissolved in methylene chloride, the solution was dried (MgSO4) and the solvent was evaporated under reduced pressure. The residue was dry column chromatographed over silica gel, using a 2:4:1 v:v:v mixture of hexane, ethyl acetate and tetrahydrofuran as eluent. The third fraction (in order of increasing polarity) was identified as a 3/1 trans/cis mixture of diastereoisomers of tetrahydro-6-phenyl-2H-pyran-3-ol (4D), a liquid, b.p.: not determined.

0.85 g of triethylamine was added to a solution of 1.2 g of 4D in 15 ml of methylene chloride at room temperature. Then, under a nitrogen atmosphere at 23° C., 0.66 g of acetyl chloride was added slowly, the temperature rising slowly to 40° C. The mixture was refluxed for 6 hours, cooled, diluted with 50 ml of methylene chloride, washed successively with water, sodium bicarbonate solution, and saturated sodium chloride solution, dried and stripped of solvent. The residue was adsorbed on a preparative silica gel plate with a 1:3 v:v tetrahydrofuran/methylene chloride mixture and chromatographed using a 4:16:80 v:v:v mixture of tetrahydrofuran, ethyl acetate and hexane as eluent. Two fractions, one an amber oil, the other a yellow oil, were obtained. The yellow oil was identified as tetrahydro-6-phenyl-2H-pyran-3-ol acetate cis isomer (4E).

0.6 mg of sodium methoxide was added to a solution of 0.25 g of 4E in 2.5 ml of methanol at room temperature. The resulting solution was stirred at room temperature for a few minutes, warmed to 45° C. and stirred at that temperature for 1 hour, refluxed (65° C.) overnight, filtered (florisil) and stripped of solvent. The residue was dried by diluting with methylene chloride and stripping the solvent, to give tetrahydro-6-phenyl-2H-pyran-3-ol cis isomer (4F), as a liquid, b.p.: not determined.

4F was converted to 4, as a liquid, b.p.: not determined, by the procedures described in Example 1 for converting 1A to 1.

EXAMPLE 5

2-((2-ethoxyethoxy)methyl)-tetrahydro-5-(phenylmethoxy)-2H-pyran cis isomer (5)

13.80 g of a 50% oil dispersion of sodium hydride was washed with pentane to remove the oil and the sodium hydride was suspended in 100 ml of dimethylformamide. In a nitrogen atmosphere, with the temperature being held at 40° C. by cooling, a solution of 28.50 g of 3,4-dihydro-2H-pyran-2-methanol in 50 ml of dimethylformamide was added drop by drop to the stirred suspension. After 45 minutes, a solution of 42.08 g of 2-bromoethyl ethyl ether in 50 ml of dimethylformamide was added drop by drop to the mixture at room temperature. The mixture was stirred for 20 hours, then was partially stripped of solvent, and the residue was treated with a mixture of equal volumes of water and methylene chloride. The two liquid phases were separated; the organic phase was washed with water, saturated sodium chloride solution, dried (MgSO4) and stripped of solvent. The residue was vacuum distilled. The fraction boiling at 51° C., 0.04 Torr., was identified as 2-((2-ethoxyethoxy)methyl)-3,4-dihydro-2H-pyran (5A).

2.5 ml of borane-dimethyl sulfide complex was added drop by drop to a stirred solution of 10.00 g of 5A in 30 ml of hexane under a nitrogen atmosphere at 2°-5° C. After 2 hours at 0°-10° C., 4 ml of ethanol was added. The solvent then was stripped, and the residue was dissolved in 30 ml of tetrahydrofuran. At −2° to +6° C. under a nitrogen atmosphere, 10.72 ml of 10% sodium hydroxide solution was added in portions to the stirred mixture. Then at 15°-40° C., 6.4 ml of 30% hydrogen peroxide solution was added drop by drop. The resulting mixture was warmed to 45° C. and held there for 45 minutes, then stripped of solvent. The residue was slurried with ethyl acetate. The mixture was filtered, and the filtrate was dried (MgSO4) and stripped of solvent. The residue was vacuum distilled to give 6-((2-ethoxyethoxy)methyl)tetrahydro-2H-pyran-3-ol (5B), b.p.: 110°-112° C., 0.07 Torr.

5 was prepared as a liquid, boiling point not determined, by treating 5B with benzyl chloride according to the procedure described in the last paragraph of Example 1.

The crude product was chromatographed (high pressure liquid) over silica gel, using as eluents one liter each, in sequence, of nine liquids: hexane, then eight mixtures of ethyl acetate and hexane, the volume ratios of the two components in the mixtures being, respectively: 100/900; 200/800; 200/800; 280/720; 400/600; 500/500; 600/400; 700/300. Five sets of fractions were collected. The third set was the trans isomer; the fifth set was the cis isomer, i.e., 5.

EXAMPLES 6-10

By the procedures described in Example 5, the following further individual species of the invention were prepared:

2-(butoxymethyl)tetrahydro-5-(phenylmethoxy)-2H-pyran, cis isomer (6), as a liquid, b.p.: 130° C., 0.1 Torr.

2-(butoxymethyl)tetrahydro-5-(2-fluorophenylmethoxy)-2H-pyran, cis isomer (7), as a liquid, b.p.: 123° C., 0.1 Torr.

2-((2-ethoxyethoxy)methyl)-tetrahydro-5-(2-fluorophenylmethoxy)-2H-pyran cis isomer (8), as a liquid, b.p.: 150° C., 0.1 Torr.

2-((2-(2-ethoxyethoxy)ethoxy)methyl)-tetrahydro-5-(phenylmethoxy)-2H-pyran cis isomer (9), as a liquid, b.p.: not determined. In this case, in the first step, instead of the bromoethyl ether, there was used 2-(2-ethoxyethoxy)ethyl p-toluenesulfonate, prepared by reacting 2-(2-ethoxyethoxy)-ethanol and p-toluenesulfonyl chloride in the presence of sodium hydride, and tetrahydrofuran as solvent.

2-((2-(2-ethoxyethoxy)ethoxy)methyl)-5-(2-fluorophenylmethoxy)-tetrahydro-2H-pyran cis isomer (10), as a liquid, b.p.: not determined.

EXAMPLE 11

2,2-bis(2-ethoxymethyl)tetrahydro-5-(phenylmethoxy)-2H-pyran (11)

225 g of acrolein was placed in a bomb, together with 72 g of toluene and 3 g of hydroquinone. The sealed bomb was warmed to and held at about 180° C. for 3 hours. Then the contents of the bomb were removed and stripped of solvent. Small amounts of potassium carbonate and hydroquinone were added to the residue. The residue was vacuum distilled and redistilled on a kugelrohr apparatus to give the thermal dimer of acrolein (11A), as a liquid, b.p.: 80° C., 11 Torr.

56 g of 11A was added drop by drop to 101.0 g of 37% aqueous formaldehyde. 46.0 g of 50% aqueous sodium hydroxide was added drop by drop to the stirred mixture at room temperature under a nitrogen atmosphere, the temperature of the mixture rising to 50° C. The mixture was heated to and held at 60° C. for 1.5 hours, then was cooled and extracted with n-butanol. A small amount of potassium carbonate was added to the extract phase, and the solvent was partially stripped. The mixture was held in a refrigerator overnight, then was filtered. The solvent was stripped from the filtrate to give 3,4-dihydro-2,2-bis(hydroxymethyl)-2H-pyran (11B), as a heavy brown oil.

10.56 g of a 50% dispersion of sodium hydride in oil was washed with pentane to remove the oil, and the sodium hydride was suspended in 80 ml of dimethylformamide. Under a nitrogen atmosphere, at 20° C., 14.40 g of a solution of 11B in 100 ml of dimethylformamide was added to the stirred suspension. The resulting mixture was cooled to about 12° C. and a solution of 62.40 g of ethyl iodide in 50 ml of dimethylformamide was added, drop by drop. The mixture was diluted with twice its volume of water and extracted with ethyl acetate. The extract was washed with water and saturated sodium chloride solution, dried (MgSO4) and stripped of solvent. The extract was vacuum distilled to give 3,4-dihydro-2,2-bis((2-ethoxy)methyl)-2H-pyran (11C) as a liquid, b.p.: 38° C., 0.08 Torr.

11C was converted to 11, as a liquid, b.p.: not determined, by the procedures described in Example 1.

EXAMPLE 12

2-((2-butoxy)methyl)-2,5-dimethyl-tetrahydro-5-(phenylmethoxy)-2H-pyran (12)

3.12 g of sodium borohydride was added to a rapidly stirred mixture of 140 ml of ether and 70 ml of water under a nitrogen atomosphere. To the resulting solution, a solution of 21.0 g of 3,4-dihydro-2,5-dimethyl-2H-pyran-2-carboxaldehyde (U.S. Pat. No. 2,479,283) in 42 ml of ether was added drop by drop. After 30 minutes, 21 ml of acetone was added. After 5 more minutes, the mixture was doubled in volume with a saturated solution of potassium carbonate and extracted with ether. The extract was washed with saturated sodium chloride solution, dried (sodium sulfate) and stripped of solvent to give 3,4-dihydro-2,5-dimethyl-2H-pyran-2-methanol (12A), as a pale green liquid, b.p.: not determined.

By the alkylation, reduction and benzylation procedures described in Example 11, 12A was converted to 12, as a liquid, b.p.: not determined.

EXAMPLE 13

By the procedures described in Example 11, the 5-(2-fluorophenylmethoxy) congener of 11, (13) was prepared as a liquid, b.p.: 130° C., 0.1 Torr.

EXAMPLES 14-15

By the general procedures described in Example 11, there were prepared the following:

2,2-bis-((2-(2-ethoxyethoxy)ethoxy)methyl)-5-(phenylmethoxy)-tetrahydro-2H-pyran (14), as liquid, b.p.: 185° C., 0.1 Torr., and the 5-(2-fluorophenylmethoxy) congener thereof, (15), as a liquid, b.p.: not determined.

EXAMPLES 16 AND 17

A solution of 100 g of 3-buten-2-one in 100 ml of toluene stabilized with 1 g of hydroquinone was heated to 200° C. in a steel pressure vessel and held at that temperature for 4 hours. The resulting mixture was distilled under reduced pressure to give 2-acetyl-3,4-dihydro-6-methyl-2H-pyran (16A), as a liquid, b.p.: 38°-42° C., 0.02 Torr.

A solution of 20.00 g of 16A in 40 ml of ethyl alcohol was added drop by drop to a solution of 2.71 g of sodium borohydride in 130 ml of ethyl alcohol and 65 ml of water, at 19°-23° C. After 30 minutes, 40 ml of acetone was added drop by drop. After 5 additional minutes, the reaction mixture was diluted with an equal volume of water, saturated with potassium carbonate, and extracted with ether. The extract was washed with saturated sodium chloride solution, dried (Na2SO4) and stripped of solvent. Some water remained in the residue. 100 ml of acetone was added to the residue; the solution was dried (Na2SO4) and stripped of solvent to give 2-(1-hydroxyethyl)-3,4-dihydro-6-methyl-2H-pyran (16B), as a liquid, b.p.: not determined.

2-(1-(2-ethoxyethoxy)ethyl)-5-hydroxy-tetrahydro-6-methyl-2H-pyran (16C) was prepared from by the alkylation and hydroxylation procedures described in Example 11. Direct benzylation of this alcohol, by the procedures already described, could lead to a variety of products, the cis-isomer being only one of them. Therefore, the alcohol was treated as follows:

A solution of 21.67 g of dimethyl sulfoxide in 65 ml of methylene chloride was added drop by drop to a solution of 16.17 g of oxalyl chloride in 260 ml of methylene chloride, at about −50° C. under a nitrogen atmosphere. After 10 minutes, a solution of 26.85 g of 16C in 130 ml of methylene chloride was added drop by drop, at a temperature of −55° to −50° C. After 20 minutes, 58.45 g of triethylamine was added drop by drop, at −60° to −50° C. The mixture was allowed to warm, and at 12° C., 320 ml of water was added. After 10 minutes, the layers were separated. The organic layer was dried (MgSO4) and stripped of solvent. The residue was filtered and stripped of solvent. The residue was vacuum distilled at 87° C., 0.10 Torr., to give 2-(1-(2-ethoxyethoxy)ethyl)-tetrahydro-6-methyl-2H-pyran-5-one (16D).

A solution of 9.2 g of 16D in 5 ml of tetrahydrofuran was added drop by drop to a solution of 50 ml of a 1 M solution of L-selectride (lithium tri-sec-butyl borohydride) in tetrahydrofuran under a nitrogen atmosphere at −70° C. The resulting mixture was stirred for one hour at −70° C., then allowed to warm to room temperature and stirred for one hour. Then 5.5 ml of water was added, followed by addition, in sequence, of 11 ml of ethanol, 40 ml of 10% sodium hydroxide solution and 17.6 ml of 30% hydrogen peroxide solution, the temperature of the mixture being held below 40° C. The mixture was stirred for one hour, then saturated with potassium carbonate, and extracted with a 1:1 v:v mixture of ether and tetrahydrofuran. The extract was dried (MgSO$_4$) and stripped of solvent. The residue was chromatographed on silica gel using a 4:30:66 v:v:v mixture of tetrahydrofuran, ethyl acetate and hexane as eluent to give a pale yellow liquid; GLC showed two close-set peaks. The liquid was identified as a 9:1 mixture of isomers of 16C (16E).

16E was benzylated by the procedure shown in Example 1 to give:

2-(1-(2-ethoxyethoxy)ethyl)-tetrahydro-5-(phenylmethoxy)-6-methyl-2H-pyran, higher $R_f$ mixture of stereoisomers (16), as a liquid, b.p.: not determined;

Same compound, lower $R_f$ mixture of stereoisomers (17), as a liquid, b.p.: 110° C., 0.05 Torr.

EXAMPLE 18

5,7-dimethyl-4-(phenylmethoxy)-6,8-dioxabicyclo(3.2.1)octane, mixture of diastereomers (18)

A solution of 11.60 g of 16B in 25 ml of methylene chloride was added drop by drop to a stirred solution of 16.44 g of m-chloroperoxybenzoic acid in 150 ml of methylene chloride under a nitrogen atmosphere at 3° C.±10° C. The mixture was allowed to warm to room temperature and after 2 hours was washed with 800 ml of 25% aqueous potassium carbonate solution and saturated aqueous sodium chloride solution, dried (MgSO$_4$) and stripped of solvent. The residue was chromatographed (high pressure liquid) over silica gel, using in sequence one liter each of six liquids: hexane, and five mixtures of ethyl acetate and hexane, as eluents, the volume ratios of the two components in the mixtures being, respectively: 210/790; 400/600; 400/600; 560/440; 800/200. One set of fractions was collected and stripped of solvent to give 5,7-dimethyl-4-hydroxy-6,8-dioxabicyclo(3.2.1)octane (18A), as a liquid, b.p.: not determined.

18A was treated with benzyl chloride, by the procedure described for treatment of 1A, to give 18, as a liquid, b.p.: 145° C., 0.06 Torr.

EXAMPLES 19 AND 20

By the procedures described in Example 18, there were prepared:

5,7-dimethyl-4-((2-fluorophenyl)methoxy)-6,8-dioxabicyclo(3.2.1)octane, higher $R_f$ mixture of stereoisomers (19), as a liquid, b.p.: not determined.

Same compound, lower $R_f$ mixture of stereoisomers (20), as a liquid, b.p.: not determined.

Compounds of Formula I have been found to be useful for killing unwanted plants, being active with respect to both broad-leaved plants and grasses, in most cases being more effective when applied preemergence (applied to the soil before the plants have sprouted), than when applied postemergence (applied to the foliage of the growing plants).

Accordingly, the invention includes a method of killing unwanted plants which comprises applying to the locus an effective amount of a compound of Formula I. Likewise, the invention also includes herbicidal compositions comprising a carrier or a surface-active agent, or both a carrier and a surface-active agent, and, as active ingredient at least one compound of Formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates, for example, natural silicas such as diatomaceous earth; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as, for example, isopropanol, glycols; ketones such as, for example, acetone, methyl ethyl ketone, methyl isobutyl ketone and cyclohexanone; ethers; aromatic hydrocarbons such as, for example, benzene, toluene and xylene; petroleum fractions such as, for example, kerosene, light mineral oils; chlorinated hydrocarbons, such as, for example, carbon tetrachloride, perchloroethylene, trichloroethane, including liquefied normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3-10% by weight of a dispersing agent, 15% of a surface-active agent and where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½-10% by weight of toxicant. Granules are usually prepared to have a size between 10 and 100 BS mesh (1.676-0.152 mm), and may be manufactured by agglomeration or impregnation techniques. Generally, granules will contain ½-25% by weight toxicant and 0-1% by weight of additives such as stabilizers, slow release modifiers and binding agents. Emulsifiable concentrates usually contain, in addition to the solvent and, when necessary, cosolvent, 10-50% weight per volume toxicant, 2-20% weight per volume emulsifiers and 0-20% weight per volume of appropriate additives such as stabilizers, penetrants and corrosion inhibitors. Suspension concentrates are compounded so as to obtain a stable, non-sedimenting flowable product and usually contain 10-75% weight toxicant, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

Protection of a locus or area from undesirable plants is effected by applying a compound of Formula I, ordinarily in a composition of one of the aforementioned types, to the soil in which seeds of the unwanted plants are present, or to the foliage of the plants. The active compound, of course, is applied in an amount sufficient to exert the desired action.

The amount of compound of the invention to be used in controlling undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kilograms per hectare of the compound of Formula I will be satisfactory.

EXAMPLES OF HERBICIDAL ACTIVITY

In the following examples, the species of plants that were tested were:

Barnyardgrass (watergrass)—*Echinochloa crus-galli*
Large crabgrass—*Digitaria sanguinalis*
Downy brome—*Bromus tectorum*
Yellow foxtail—*Sectaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnsongrass—*Sorghum halepense*

Test Procedures

The preemergence (soil) herbicidal activity of compounds of the invention was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyard grass and cress seeds contained one milligram of the test compound per tube, and contained 0.1 milligram of the test compound per each tube containing the seeds of the other plants. The dosages were approximately 22 and 2.2 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
|---|---|
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

The postemergence (foliar) herbicidal activity of compounds of the invention was evaluated by spraying 10-day-old large crabgrass plants, 13-day-old redroot pigweed plants, 6-day-old downy brome plants in some cases, 6-day-old Johnsongrass plants in other cases, 9-day-old velvetleaf plants, 9-day-old yellow foxtail plants and 9-day-old sicklepod plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days and the effect of the test compound was then evaluated visually, the results being rated on the 0 to 9 scale described above.

Results of the preemergence and postemergence herbicidal activity tests conducted on the compounds of the invention are set forth in Table I below.

TABLE I

| | HERBICIDAL ACTIVITY | | | | | | | | | | | |
|---|---|---|---|---|---|---|---|---|---|---|---|---|
| | Preemergence | | | | | | Postemergence | | | | | |
| Compound | Barnyard-grass | Garden cress | Downy brome | Velvet-leaf | Yellow foxtail | Sickle-pod | Crab-grass | Pig-weed | Johnson-grass | Velvet-leaf | Yellow foxtail | Sickle-pod |
| 1  | 6 | 9 | 9 | 3 | 7 | 6 | 0 | 2 | 2 | 0 | 0 | 0 |
| 2  | 9 | 6 | 9 | 3 | 8 | 6 | 2 | 4 | 3 | 0 | 0 | 2 |
| 3  | 7 | 7 | 7 | 1 | 6 | 0 | 6 | 6 | 4 | 3 | 5 | 7 |
| 4  | 8 | 6 | 5 | 3 | 5 | 4 | 3 | 6 | 2 | 2 | 5 | 2 |
| 5  | 9 | 7 | 9 | 2 | 8 | 0 | 6 | 5 | 0 | 2 | 1 | 1 |
| 6  | 9 | 6 | 9 | 3 | 8 | 3 | 6 | 4 | 0 | 1 | 0 | 0 |
| 7  | 9 | 7 | 9 | 2 | 8 | 2 | 8 | 7 | 2 | 2 | 2 | 2 |
| 8  | 9 | 7 | 9 | 0 | 9 | 6 | 7 | 3 | 0 | 2 | 2 | 2 |
| 9  | 9 | 6 | 8 | 3 | 8 | 3 | 2 | 3 | 0 | 2 | 0 | 0 |
| 10 | 9 | 7 | 8 | 3 | 8 | 5 | 6 | 3 | 2 | 2 | 0 | 3 |
| 11 | 9 | 4 | 8 | 2 | 8 | 3 | 6 | 3 | 2 | 0 | 2 | 2 |
| 12 | 9 | 7 | 9 | 2 | 3 | 4 | 6 | 6 | 0 | 3 | 0 | 4 |
| 13 | 9 | 6 | 8 | 2 | 8 | 3 | 8 | 5 | 0 | 3 | 0 | 3 |
| 14 | 9 | 2 | 5 | 0 | 5 | 2 | 5 | 3 | 0 | 0 | 5 | 2 |
| 15 | 7 | 3 | 7 | 0 | 7 | 2 | 6 | 5 | 0 | 0 | 3 | 4 |
| 16 | 9 | 7 | 7 | 7 | 8 | 4 | 7 | 6 | 3 | 4 | 0 | 3 |
| 17 | 9 | 7 | 9 | 7 | 8 | 4 | 8 | 7 | 4 | 6 | 4 | 4 |
| 18 | 9 | 7 | 6 | 5 | 8 | 5 | 3 | 5 | 0 | 2 | 8 | 2 |
| 19 | 9 | 7 | 9 | 3 | 8 | 3 | 2 | 3 | 0 | 2 | 0 | 2 |
| 20 | 8 | 7 | 8 | 6 | 8 | 6 | 2 | 3 | 0 | 2 | 0 | 0 |

We claim:

1. A compound of the formula:

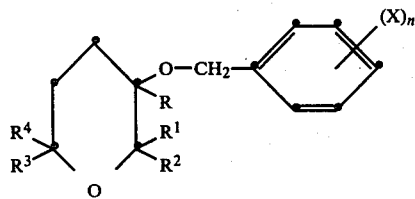

wherein R is hydrogen, phenyl or alkyl of from one to four carbon atoms, $R^1$ is hydrogen or alkyl of from one to four carbon atoms, $R^2$ is hydrogen, $R^3$ is hydrogen, alkyl of from one to four carbon atoms, phenyl or is a moiety $R^5$—O+CH$_2$CH$_2$—O)$_{\overline{m}}$CH($R^6$)—, wherein m is zero, one or two, $R^4$ is hydrogen, alkyl of from one to four carbon atoms, or a moiety $R^5$—O((CH$_2$CH$_2$)—O)$_{\overline{m}}$CH($R^6$)—, $R^5$ is alkyl of from one to six carbon atoms and $R^6$ is hydrogen or alkyl of one to four carbon atoms, with the proviso that $R^3$ and $R^2$ together can represent the moiety —C($R^7$)$_2$—O—, wherein $R^7$ is hydrogen or alkyl of from one to four carbon atoms, $R^2$ representing the oxa (—O—) oxygen therein, X is halogen, and n is zero, one or two.

2. A herbicidal composition comprising a herbicidal amount of a compound of claim 1, and at least one surface-active agent or carrier therefor.

3. A method for killing unwanted plants at a locus which comprises applying to the locus to be protected a herbicidal amount of a compound of claim 1 or a composition containing it.

* * * * *